United States Patent [19]

Kang et al.

[11] 4,326,052
[45] Apr. 20, 1982

[54] DEACETYLATED POLYSACCHARIDE S-60

[75] Inventors: Kenneth S. Kang, LaJolla; George T. Colegrove; George T. Veeder, both of San Diego, all of Calif.

[73] Assignee: Merck & Co., Inc., Rahway, N.J.

[21] Appl. No.: 178,053

[22] Filed: Aug. 14, 1980

Related U.S. Application Data

[63] Continuation-in-part of Ser. No. 47,505, Jun. 8, 1979, abandoned, which is a continuation-in-part of Ser. No. 966,538, Dec. 4, 1978, abandoned.

[51] Int. Cl.³ .......................... C07H 1/00; C07H 1/08
[52] U.S. Cl. ............................ 536/1; 8/561; 8/563; 71/DIG. 1; 106/205; 106/209; 260/112 R; 252/316; 252/352; 252/356; 426/573; 426/589; 426/658; 435/104; 435/243; 536/114; 536/119
[58] Field of Search ............... 536/1, 114; 260/112 R

[56] References Cited

U.S. PATENT DOCUMENTS

| | | | |
|---|---|---|---|
| 3,000,790 | 9/1961 | Jeanes et al. | 536/1 |
| 3,516,983 | 6/1970 | Colegrove | 536/1 |
| 4,119,491 | 10/1978 | Wellington | 536/114 |
| 4,154,822 | 5/1979 | Polimeni et al. | 536/1 |

FOREIGN PATENT DOCUMENTS 2396019  1/1979  France .................................. 536/1

OTHER PUBLICATIONS

Chem. Abst., vol. 86, No. 1, Jan. 3, 1977, p. 321, abstr. 3575(e).

*Primary Examiner*—Johnnie R. Brown
*Attorney, Agent, or Firm*—Gabriel Lopez; Hesna J. Pfeiffer

[57] ABSTRACT

Deacetylated Polysaccharide S-60, prepared by deacetylating the polysaccharide S-60 produced by fermentation of *Pseudomonas elodea*, ATCC 31461, has valuable properties in both the clarified and non-clarified form, and is useful as an agar substitute or a shapeable room deodorant.

The non-clarified deacetylated gum contains about 17% protein and principally carbohydrate, which comprises glucuronic acid ($\sim$13% based on wt. gum) and the neutral sugars rhamnose and glucose in the approximate molar ratio 3:2.

The clarified, deacetylated gum contains mostly carbohydrate and no more than about 2% protein.

4 Claims, No Drawings

DEACETYLATED POLYSACCHARIDE S-60

CROSS-REFERENCE

This is a continuation-in-part of copending U.S. Ser. No. 47,505, filed June 8, 1979, now abandoned, which is a continuation-in-part of U.S. Ser. No. 966,538, filed Dec. 4, 1978, now abandoned.

Heteropolysaccharide S-60 is disclosed and claimed in a copending application filed on even date herewith Ser. No. 178,054 which is a continuation-in-part of U.S. Ser. No. 47,598, filed June 8, 1979, now abandoned, which is a CIP of U.S. Ser. No. 966,531, filed Dec. 4, 1978, now abandoned.

BACKGROUND OF THE INVENTION

Compound S-60 may be prepared by fermentation of a suitable nutrient medium with a hitherto undescribed organism. Based on extensive taxonomic studies, the organism has been designated to be a new species, *Pseudomonas elodea*. An unrestricted permanent deposit of an organism of this species employed in making our heteropolysaccharide was made with the American Type Culture Collection on Nov. 21, 1978, under Accession No. ATCC 31461.

Various classification keys for the genus Pseudomonas and the culture descriptions of *Pseudomonas* species are found in the 7th Edition of Bergey's Manual (Breed et al., (1957)) and the 8th Edition of Bergey's Manual (Doudoroff et al., (1974), as well as by other schools in various publications; Hugh and Gilardi, 1974, Pseudomonas, *Manual of Clinical Microbiology*, 2nd ed., Lennette et al., Eds., pp. 250–269. American Society for Microbiology, Washington, D.C.; Weaver et al., 1972, Identification of Unusual Pathogenic Gram-Negative Bacteria, E. O. King, Center for Disease Control, Atlanta; Iizuka et al., 1963, Attempt at Grouping the Genus Pseudomonas, *J. Gen. Appl. Microbiology* 9:73–82; and Hendric et al., 1966, Identification of Certain Pseudomonas Species, *Identification Methods for Microbiologists*, Part A, Gibbs et al., Eds., pp. 1–7, Academic Press, New York.

These keys and descriptions were searched for a Pseudomonas species having morphological and cultural characteristics similar to those of ATCC 31461. The following considerations make the assignment of a new Pseudomonas species justified and necessary.

DESCRIPTION OF THE STRAIN

1. Characteristics of Cell Morphology

Single cells, straight or often curved, generally 0.6–0.8 by 2.0–3.0 μm, often with tapered end. The older cultures become larger and longer (0.8–1.0 by >3 μm), misshaped cells and pleomorphism appear, especially on media with limited amount of carbohydrates. On the contrary, cells keep rather consistent rod shapes when grown on media with carbohydrates, but again, most cells become large and pleomorphism develops during prolonged incubation. Gram-negative, non-capsulated, poly-β-hydroxybutyrate and polyphosphate granules are seen especially in cultures of nitrogen-deficient media. Motile by polar multitrichous flagellation; one to four flagella are inserted at the polar end and occasionally subpolar insertion may be seen.

2. Characteristics of Colonial Morphology

On nutrient agar plates, small (0.8–1.1 mm in diameter) and large (3.2–3.5 mm in diameter) colonies appear. They are yellow carotenoid pigmented, smooth, round, and convex to pulvinate. Large colonies often have a concentric wrinkle. The surface of these colonies has a hard but not viscid texture and entire colonies are removed if pushed by a loop. On YM agar plates, only one type of relatively large (~6–7 mm in diameter) yellow, round, smooth, slimy and convex colonies appear. Slimy elastic membranes form on the surface of these colonies and whole surface membranes (of colonies) can be removed. The secondary growth may occur around the edge of the original colonies. The color of these colonies is darker yellow towards the center than the edge and concentric color formation appeared. In addition to the intracellular yellow carotenoid pigment(s), diffusible brown pigment developed as a result of autooxidation after prolonged incubation. This phenomenon is more easily recognized on Nutrient agar. No fluorescent pigment was produced.

3. Physiological and Biochemical Characteristics

The growth range of the strain S-60 is about 20° C. to 41° C. No growth occurs at 4° C. 3.0% NaCl is sufficient to inhibit the growth and the strain is capable of growth at pHs between 5 and 11.

Acid, but no gas is produced from almost all carbohydrates but not from polyalcohols. Urease may be produced. MR, VP, and indole tests were all negative. Argine dihydrolase, lysine and ornithine decarboxylase are not produced. Acid and reduction occurs in litmus milk. Lipolytic egg yolk reaction is negative. Gelatin is weakly hydrolyzed but not casein, starch, alginate, pectin, cellulose, chitin and DNA.

4. Susceptibility to Antibiotics

The strain is very susceptible to Kanamycin, Neomycin, Chlortetracycline, Erythromycin, but not Streptomycin and Penicillin.

5. Nutritional Characteristics

Organic growth factors are not required and ammonium salts serve as sole nitrogen source. At least 35 organic compounds were utilized, those being most carbohydrates other than D-ribose, starch, 2-ketogluconate, and mucate. In addition, acetate, caproate, caprylate, pelargonate, succinate, azelate, L-malate, DL-β-hydroxybutyrate, pyruvate, ethanol, n-propanol, p-hydroxybenzoate, phenylacetate, L-α-alanine, L-threonine, L-leucine, DL-isoleucine, L-aspartate, L-glutamate, and L-tyrosine were utilized.

6. The G+C Content of the DNA

Evaluation of the DNA resulted in the mole % to be ~68 (by Tm).

TABLE 1

| Biochemical and Other Miscellaneous Tests Employed for the Strain S-60 | | | |
|---|---|---|---|
| Oxidase: | | | |
| Kovac's | + (weak) | Hydrolysis of: | |
| Pathotech | + (weak) | Gelatin | + (weak) |

TABLE 1-continued

Biochemical and Other Miscellaneous Tests Employed for the Strain S-60

| | | | |
|---|---|---|---|
| Catalase | + | Casein | − |
| OF medium: | | Starch | − |
| Oxidative | + | Tween 80 | + |
| Fermentative | − | Pectin | − |
| Gas from glucose | − | Alginate | − |
| H$_2$S production: TSI | − | Cellulose | − |
| from cystine | + | Chitin | − |
| Ammonium from peptone | + | DNA | − |
| β-Galactosidase (ONPG) | + (API) | Esculin | + |
| Arginine dihydrolase | − | | |
| Lysine decarboxylase | − | Growth on various media: | |
| Ornithine decarboxylase | − | EMB agar | − |
| Tryptophan deaminase | − | MacConkey agar | − |
| Phenylalanine deaminase | − | SS agar | − |
| Urease | +/± | Mannitol salt agar | − |
| Indole | − | TCBS agar | − |
| MR test | − | Tinsdale tellurite | |
| VP test | − | blood agar | + |
| Nitrate reduction | − | Pseudosel agar | − |
| Nitrate reduction | − | | |
| Denitrification | − | Pigment production: | |
| N$_2$-fixation: | | King A medium | − |
| Growth in Burk's medium | + | King B medium | − |
| Nitrogenase activity | − | | |
| Malonate (oxidation) | − | Dye reaction: | |
| Phosphatase | + | Congo red | − |
| Haemolysis (sheep blood) | − | Nite blue | − |
| Litmus milk: acid, reduction only | | | |
| 3-ketolactose production | − | | |
| Survival at 60° C. for 30 min. | − | | |
| TSI: | | | |
| Slant | color no change | | |
| Butt | color no change | | |
| Gas | − | | |
| Egg Yolk Reaction | − | | |

FERMENTATION CONDITIONS

Heteropolysaccharide S-60 is produced during the aerobic fermentation of suitable aqueous nutrient media under controlled conditions via the inoculation with the organism of the *Pseudomonas elodea* species. The media are usual media, containing source of carbon, nitrogen and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depend in part upon the other ingredients of the medium but, in general, the amount of carbohydrate usually varies between about 2% and 4% by weight of the medium. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles or tomato paste and the like. The sources of nitrogen, either alone or in combination, are used in amounts ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and like ions. Also included are trace metals such as cobalt, manganese, iron and magnesium.

It should be noted that the media described in the examples are merely illustrative of the wide variety of media which may be employed, and are not intended to be limitative.

The fermentation is carried out at temperatures ranging from about 25° C. to 35° C.; however, for optimum results it is preferable to conduct the fermentation at temperatures of from about 28° C. to 32° C. The pH of the nutrient media for growing the Pseudomonas culture and producing the polysaccharide S-60 can vary from about 6 to 8.

Although the novel polysaccharide S-60 is produced by both surface and submerged culture, it is preferred to carry out the fermentation in the submerged state.

A small scale fermentation is conveniently carried out by inoculating a suitable nitrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-60 is particularly suited for the preparation of large quantities.

S-60 is produced at a conversion efficiency of about 50%, resulting in a very high viscosity beer (4,000 to 8,000 cP). The product is recovered from the fermentation medium by precipitation with a suitable alcohol, such as isopropanol.

HETEROPOLYSACCHARIDE S-60

The heteropolysaccharide produced by *P. elodea* is composed of about 50% carbohydrate and 50% insoluble material which contains protein (10 to 15% based on total weight).

The carbohydrate portion contains 3 to 4.5% O-acetyl groups as the O-glysosidically linked ester, about 11% glucuronic acid (both based on total weight of the heteropolysaccharide) and the neutral sugars rhamnose and glucose. The approximate molar ratio of rhamnose to glucose is 3:2. The rhamnose and glucose are linked 1,4 and the negative specific rotation ($[\alpha]_{589}^{25} = -45\%$) of the deacetylated, clarified material indicates that the majority of the glycose units are $\beta$-linked. The heteropolysaccharide is anionic.

The acetyl content of 4.5% was determined by treating a 0.2% aqueous solution of S-60 gum with an alkaline, hydroxylamine reagent followed by treatment with an acidic ferric chloride reagent [S. Hestrin (1949) *J. Biol. Chem.* 180 249–261].

The neutral sugars of polysaccharide S-60 were determined by dissolving ten mg. of the product in 2 ml 2N $H_2SO_4$, and the mixture is heated at 100° C. for 4 hours. The resulting solution is cooled, neutralized with barium hydroxide and the pH is brought to 5–6 with solid carbon dioxide. The resulting precipitate of barium sulfate is removed by centrifugation and the supernatent is concentrated to a syrup under reduced pressure. The sugars in the hydrolysate are tentatively identifed by gasliquid chromatography of their aldononitril acetate derivatives on a Hewlett-Packard Model 5750 chromatograph using 3% by weight OV-225 on 80/100 mesh Gas Chrome Q at 210° C. The sugars are identified and quantitated by comparison with authentic standards [J. K. Baird, M. J. Holroyde, and D. C. Ellwood (1973) *Carbohydr. Res.* 27 464–467].

The various neutral sugars of the polysaccharides were also characterized by use of descending paper chromatography on Whatman No. 1 chromatography paper using as the solvent the upper layer of pyridine: ethyl acetate-water (2:5:5). Chromatograms were stained using silver nitrate dip and acid analine phthalate spray reagent. Component sugars were identified by co-chromatography with sugar standards and by the specific-color reaction with the aniline phthalate reagent.

The glycosidic linkages have been determined by methylation of the purified polysaccharide followed by hydrolysis and quantitation of the O-methyl sugars as the alditol acetate derivatives. The derivatives were separated and identified by gas liquid chromatography—mass spectrometry using a Hewlett-Packard Model 5992 GC/MS fitted with 1.5 ft. glass columns containing 3% OV-225 at 170° C. The derivatives of 2,3 di-o-methylrhamnose and 2, 3, 6-tri-o-methylglucose were identified by comparing the GC/MS spectra and relative retention times with those of known O-methyl sugar standards and with published data.

The uronic acid content of the polysaccharide was determined by two separate methods. In one method the sample was decarboxylated with 19% hydrochloric acid and the liberated carbon dioxide was trapped in standard sodium hydroxide and determined by back titration [B. L. Browning (1967) Methods of Wood Chemistry II, 632–633] and by the carbazole colorimetric method [T. Bitter and H. M. Muir (1962) Anal. Biochem. 4 330–334].

Paper electrophoresis was used for the separation and tentative identification of the uronic acids present in the neutralized acid hydrolysate described above. Aliquots of this and known uronic acid standards were applied to Camag electrophoresis paper No. 68–011 and electrophoresis was carried out for 2.0 hours in a pH 2.7 buffer using a Camag Model HVE electrophoresis apparatus. Chromatograms were air dried and stained with silver nitrate dip reagent to locate the uronic acids being separated. Two major and one minor uronic acid spots were found. One of the major spots migrated with the same mobility as glucuronic acid ($R_{GlcA} = 1.0$) while the other major spot ($R_{GlcA} = 0.85$) and the minor spot ($R_{GlcA} = 0.73$) had lower mobility. Under these same conditions the relative mobility of known uronic acids are:

|  | $R_m$ |
|---|---|
| Glucuronic acid | 1.0 |
| Mannuronic acid | 0.96 |
| Galacturonic acid | 0.65 |
| Guluronic acid | 0.63 |

These secondary spots are interpreted as being uronic acid containing oligosaccharide, which is the result of incomplete hydrolysis. Thus all of the uronic acid is glucuronic.

An infrared spectrum of native S-60 was made on dried material in a KBr pellet. The heteropolysaccharide evidenced peaks at: 3400 cm$^{-1}$, 2950 cm$^{-1}$, 1740 cm$^{-1}$, and 1620 cm$^{-1}$ indicating hydroxyl groups, methylene groups, carbonyl groups and carboxylic acid salts.

S-60 is incompatible with methylene chloride dye, substantially insoluble in N,N-dimethylformamide, and soluble in DMSO or formamide.

A sample of S-60 shows the following elemental analysis: N-2.00%, C-42.62%, H-5.80%.

S-60 is readily soluble in water and is characterized by high viscosity at low concentration. Typical viscosities are 40–80 cP at 0.1% concentration and 1000–2000 cP at 0.5% when measured on a Brookfield LVF viscometer, 60 rpm, at 25° C., (spindles 2 and 3, respectively). The gum also has a high rheological yield point; a 1% gum solution has a working yield value of 60 dynes/cm², defined by the shear stress at a shear rate of 0.01 sec$^{-1}$ as measured using a Wells-Brookfield cone and plate viscometer in the spring relaxation mode.

Changes of pH in the range 3-11 do not substantially affect the viscosity of 0.5% solution of S-60.

The effect of temperature on the solution viscosity of S-60 is both characteristic and unusual. The viscosity of a 0.5% S-60 solution is stable in the range of 20°-70° C. and abruptly undergoes a reversible decrease when the temperature is increased above 70° C. A most significant property of S-60, both in its native state and after deacetylation is the formation of thermoreversible gels after heating and cooling. Following heating in the presence of various cations, native S-60 forms elastic or soft gels upon cooling, deacetylated S-60 produces firm, non-elastic or brittle gels. Cations especially useful in the formation of gels with S-60 are those of sodium, potassium, magnesium, calcium, barium, aluminum, and chromium.

S-60 is useful as a thickening, suspending and stabilizing agent in aqueous systems; for example, as an additive to textile printing pastes or in formulating low drift aqueous herbicide compositions, salad dressings, thickened puddings, and adhesive compositions.

DEACETYLATED, NON-CLARIFIED S-60

When the dry polymer or the fermentation broth is heated at high pH (using e.g., sodium carbonate or sodium hydroxide to pH 10) and high temperatures 90°-100° C. for 10 minutes to 45 minutes deacetylation readily occurs. The resultant deacetylated polysaccharide S-60 forms firm non-elastic or brittle gels, useful in many industrial and food applications.

The composition of the deacetylated S-60 is about the same as that of native S-60. It is composed of about 50% carbohydrate and about 50% insoluble material which contains about 17% protein (based on total weight).

The carbohydrate portion contains about 0% acetyl, 11-13% glucuronic acid (based on total weight) and the neutral sugars rhamnose and glucose in the approximate molar ratio 3:2. The rhamnose and glucose are linked 1,4 and the majority of the glycose units are β-linked.

An infrared spectrum of deacetylated S-60 made on dried material in a KBr pellet evidenced peaks at: 3400 cm$^{-1}$, 2950 cm$^{-1}$, 1740 cm$^{-1}$, 1650 cm$^{-1}$, and 1610 cm$^{-1}$.

A sample of deacetylated S-60 shows the following elemental analysis: N-2.67%, C-41.89%, H-6.07%.

One use for the deacetylated gum results from the fact that as a rigid, brittle gel, it can be molded, and used as a rigid structure, which after treatment with a suitable solution such as fragrance, finds applicability as a room deodorant or an air freshener, or the like. The deacetylated gum can also be used in gel electrophoresis, as a gelling agent for use in microtomes in electron-microscopy. The native and deacetylated gums can also be used as suspending agents for barium in radiology, confectionary products, and as impression materials in tool making, dentistry and criminology.

DEACETYLATED, CLARIFIED S-60

The composition of the clarified, deacetylated S-60 differs from the unclarified, deacetylated S-60 in that it is primarily carbohydrate, the remaining insoluble material containing no more than about 2% protein (based on total weight).

An infrared spectrum of clarified, deacetylated S-60 made on dried material in a KBr pellet evidenced peaks at: 3400 cm$^{-1}$, 2950 cm$^{-1}$, and 1600 cm$^{-1}$.

A sample of deacetylated, clarified S-60 shows the following elemental analysis: N-0.42%, C-36.85%, H-5.62%. The sample has a specific rotation:

$$[\alpha]_{589}^{25} = -45° C.$$

The deacetylated clarified gum is especially useful as an agar substitute in microbiological culture media for various clinical and non-clinical microorganisms using a wide variety of culture media. The concentration of deacetylated clarified gum necessary to replace agar is dependent upon the medium used, but is within the range of about 0.5 to about 1.25% (weight volume). Growth characteristics of microorganisms are quite similar to those on standard agar-based media.

The following detailed examples illustrate representative aspects of this invention.

EXAMPLE 1

Fermentation Procedure for Producing Heteropolysaccharide S-60

A. Culture Maintenance

*Pseudomonas elodea*, ATCC 31461, grows quite well on NA or YM agar, which are used routinely for culture maintenance. The incubation temperature is 30° C. The organism produces a yellow-orange carotinoid pigment and a brown diffusable pigment by 2-5 day's incubation.

B. Seed Preparation

Flask seeds are prepared in YM broth incubated at 30° C. When inoculated with a fresh plate culture, the YM broth cultures give good growth and gum formation by 24 hours.

The fermentation seed medium is the same as final fermentor medium, using one-gallon fermentors as seed vessels.

C. Final Fermentor Medium

The sodium- and potassium-salt form of the gum are prepared in a different media; both are described below. The organism has a definite K+ requirement which must be added to the sodium fermentation medium. (3% dextrose can also be used). 0.2% corn steep liquor is added in both media.

| Sodium Salt | Potassium Salt |
|---|---|
| 3.0% Glucose | 3.0% Glucose |
| 0.01% MgSO$_4$ . 7H$_2$O | 0.01% MgSO$_4$ . 7H$_2$O |
| 0.09% NH$_4$NO$_3$ | 0.09% NH$_4$NO$_3$ |
| 0.05% Promosoy (soy protein concentrate) | 0.05% Promosoy |
| 1 ml/L HoLe salts | 1 ml/L HoLe salts |
| 1 ppm Fe++ | 1 ppm Fe++ |
| 0.05% Na$_2$HPO$_4$ | 0.05% K$_2$HPO$_4$ |
| 10 ppm K+ | |
| pH control = NaOH | pH control = KOH |

HoLe salts are a trace element solution containing, tartrate, magnesium molybdate, CoCl$_3$, ZnCl$_2$, CuCl$_2$, boric acid, manganese chloride and ferrous sulfate.

When a low calcium product is desired, either of the media above are used with deionized water. Fermentation is complete aq. 50 hours; beer viscosity usually is 5000-8000 cp.

D. Recovery

Because of the gelling nature of the product, good fiber formation usually does not occur with ambient precipitation. However, we have found that by pasteurization at 90°–95° C. for 3 minutes (during which the thick beer heat-thins considerably) excellent fibers can be obtained by precipitation of the beer using two volumes of 99% isopropanol per volume of beer without cooling. Average yields of 1.5% gum are obtained with 3% glucose in the 20L and 70L fermentors.

E. Drying

The product is recovered and dried at 50°–55° C. for up to one hour in a forced-air tray dryer.

F. Product Quality

One-percent viscosities of the K+ salt are usually in the range of 3000 cP and for the lowcalcium sodium salt, approximately 7000 cP.

EXAMPLE 2

Deacetylation and Clarification of the Heteropolysaccharide S-60

Clarification of the gum, while not necessarily for all uses, is of value when the gum is used as an agar substitute. Clarification can be accomplished before deacetylation (in the native state) or after deacetylation. Since deacetylation uses hot caustic, and clarification is done hot, the two procedures are easily and conveniently combined. Both deaceylation and clarification can be done with the beer or the dry polymer. For deacetylation, if the beer is used, the pH is adjusted to 10 with KOH, the solution heated to 90° C. for 15 minutes, the pH adjusted to pH 7 with dilute $H_2SO_4$, then clarified.

The general procedure for both deacetyation and clarification follows:

A. A 2% solution of beer or gum is heated to 90° C.
B. The pH is adjusted to 10 with KOH.
C. The temperature of the beer or solution was maintained at 90°–95° C. for 15 minutes.
D. The pH is adjusted to 6–8 with dilute HCl or $H_2SO_4$.
E. Ten gms/liter of Super Aid were added to the material to be filtered.
F. The material was filtered through a pressure filter unit (pre-heated) with approximately a 6 mm bed of Super Aid and approximately 20–30 psi, using a filter unit with an area of 136 $cm^2$.
G. The filtrate is precipitated with isopropanol immediately to prevent gelation and the fibers dried at 50° C. for one hour or less.

When no deacetylation is necessary, the above procedure is followed, except that the pH is not raised; rather than holding at 90° C., the solution is immediately filtered, and then recovered.

Clarification is typically done on the potassium form; KCl can be added to a solution of previously made product as necessary.

EXAMPLE 3

DEACETYLATED, NON-CLARIFIED S-60

S-60 fermentation liquor is heated to 90° C. and the pH adjusted to 10 by addition of 25% KOH. The temperature is maintained for 15 minutes, followed by neutralization with concentrated HCl. This liquor is then drained from the fermentor while hot and recovered with 2 volumes of 99% IPA. The fibers of deacetylated S-60 are collected, dried at 55° C. for one hour in a forced air tray drier, and then milled to a powder.

EXAMPLE 4

CLARIFICATION OF DEACETYLATION S-60

Deacetylated heteropolysaccharide S-60 as prepared in Example 3 is reconstituted to a 1% concentration in deionized water using a Lightnin mixer for one hour followed by mixing on an Arti-Barinko with heating to 50° C. The solution is then centrifuged at 10,000 R.P.M. (GSA head) for 20 minutes in a Sorvall RC2-B refrigerated centrifuge keeping the temperature above 40° C. The supernatant is decanted off and sequentially filtered through Gelman type AN Hydrophilic Acropor membranes (293 mm) of porosities of 5μ, 3μ, 1.2μ and 0.8μ. The filtrate is added to approximately 3–4 volumes of 99% isopropanol, the fibers collected and dried briefly in the forced air tray drier at 55° C., followed by milling to a powder. The product is the deacetylated, clarified S-60 gum of this invention.

EXAMPLE 5

Heteropolysaccharide S-60 Gelling Characteristics

A compilation of data comparing the native gum and the deacetylated gum, both in the K+ form and in the Ca++ form, with carrageenan and agar follows:

| Type | Gel Nature | Melts | Sets | Hysteresis |
|---|---|---|---|---|
| Native S-60 | Very Elastic | 65–70° C. | 65–70° C. | None |
| Deacetylated S-60 | | | | |
| K+ Gel | Brittle | 90° C. | 31–48° C. | 45–60° C. |
| Ca$^{2+}$ Gel | Brittle | 90° C. | 45–50° C. | 45–50° C. |
| Kappa Carrageenan | Brittle | 40–95° C. | 25–75° C. | 15–20° C. |
| Agar* | Brittle | 60–97° C. | 32–39° C. | 60° C. |

*Bacteriological grade specs: gelling temperature range 33°–39° C., melting temperature 70° C. minimum. (Whistler's "Industrial Gums")

Minimum Gelling Concentration

| | |
|---|---|
| Kappa Carrageenan | 0.3% |
| Agar | 0.04% |
| Deacetylated S-60 (calcium gel) | 0.05% |

Note above that there is a wide range of temperatures given for setting and melting of all the various types of gels. For agar, the variations are primarily due to type of seaweed while the kappa carrageenan the potassium ion concentration determines the gel characteristics. The gels of deacetylated S-60 are primarily characterized by the degree of deacetylation. With only slight deacetylation the gels set at higher temperatures and are more elastic; in fact, a wide range of gel types from very elastic to very brittle is possible, depending on the degree of deacetylation. The gels appear to be more similar to agar than to kappa carageenan, primarily because of the large hysteresis between setting and melting temperatures. It should be emphasized that they are difficult to melt and the gel-sol transition is difficult to observe. On the other hand, the gelling temperatures can be easily defined since the gels set sharply within a few degrees from incipient gelation to solid gel.

EXAMPLE 6

Agar Replacement Using Deacetylated Clarified S-60

Several different media are prepared as follows:

Nutrient Agar

-continued (A) 0.8% Nutrient Broth (Difco)
    1.5% Agar (Difco)
(B) 0.8% Nutrient Broth (Difco)
    0.2% KCl
    0.9% S-60

Trypticase Soy Agar (A) 2.75% Trypticase Soy Broth (BBL)
    1.5% Agar (Difco)
(B) 2.75% Trypticase Soy Broth (BBL)
    0.2% KCl
    0.9% S-60

Potato Dexrose Agar (A) 2.4% Potato Dextrose Broth (Difco)
    1.5% Agar
(B) 2.4% Potato Dextrose Broth (Difco)
    0.2% KCl
    0.9% S-60

YM Agar (A) 2.1% YM Broth (Difco)
    1.5% Agar (Difco)
(B) 2.1% YM Broth
    0.2% KCl
    0.9% S-60

Brain Heart Infusion Agar (A) 3.7% BHI Broth (Difco)
    1.5% Agar
(B) 3.7% BHI Broth (Difco)
    0.2% KCl
    0.9% S-60

Burk's Agar (A)
0.0584% $K_2HPO_4$
0.0225% $KH_2PO_4$
0.0174% $K_2SO_4$
0.0164% $MgCl_2 . 6H_2O$
0.0064% $CaCl_2 . 2H_2O$
0.0005% $FeCl_3 . 6H_2O$
0.00002% $Na_2MoO_4 . 2H_2O$
0.0116% NaCl
1.0% Glucose
1.5% Agar (Difco)

(B) —Same as (A)
    0.2% KCl
    0.9% S-60

Deionized water was used for all media. The ingredients were combined (except for Burk's) and autoclaved for 15–20 minutes at 121° C. and 15 psi, cooled to 55° C., and poured into sterile petri dishes. The ingredients for Burk's were combined, except for the glucose, which was autoclaved separately, and added to the medium after autoclaving. After these nutrient plates had solidified and allowed to incubate at ambient temperature for 24 hours to check for sterility, they were streaked with the following fourteen cultures:

*Agromyces ramosus* ATCC 25173
*Arthrobacter globiformis* ATCC 8010
*Aureobasidium pullulans* NRRL YB-3861
*Azotobacter indicus var myxogenes* strain S-7 ATCC 21423
*Azotobacter vinelandii* ATCC 9047
*Beijerinckia lacticogenes* ATCC 19361
*Erwinia cartovora* ATCC 8061
*Escherichia coli* strain EG-47
*Klebsiella pneumoniae* strain S-53
*Nocardia salmonicolor* ATCC 21243 S-60
*Streptococcus faecalis*
*Trichoderma longbrachiatum* ATCC 13631
*Zoogloea ramigera* ATCC 25935

The plates were incubated at 30° C. for 3–5 days and then examined for growth. Good growth was observed for all strains on media made with S-60 and little difference in colonial morphology was noted between media made with S-60 instead of agar. These results indicate that S-60 is an excellent replacement for agar in microbiological media. The gel point for all media containing S-60, except BHI medium and TSA, was 42° C. The gel point for BHI agar and TSA was 52° C. Agar typically gels at 42°–44° C.

EXAMPLE 7

Preparation of Molded Scented Gels Using Deacetylated S-60

| (A) | | |
|---|---|---|
| 1.50% | Polysaccharide S-60 |
| 0.75% | Sodium Carbonate |
| 0.025% | Methyl p-hydroxybenzoate |
| 3.00% | Rose fragrance |
| 4.00% | Isopropanol |
| 2.00% | Ethylene glycol |
| 88.50% | Water |

The native polysaccharide S-60 is blended with sodium carbonate and preservative and dissolved in water at 70° C. The solution is then further heated to 90° C. and held at that temperature for ten minutes to deacetylate the polysaccharide. After cooling to 60° C., the fragrance dispersed in the solvents is added and the mixture placed in the usual air freshener plastic molds. When the mixture cools to 38° C., gelation occurred and a firm, self-supporting gel with good fragrance releasing properties results.

(B) A dry deacetylated polysaccharide S-60 is prepared from the fermentate beer by adjusting the pH to 10.0 with dilute sodium hydroxide and heating to 90° C. for fifteen minutes. The solution is neutralized to pH 7 with dilute hydrochloric acid, precipitated in two volumes of isopopranol, dried, and milled. A solid air freshener gel is prepared from the deacetylated product in the following manner: 3.0 grams of the deacetylated polysaccharide S-60 are blended with 1.5 grams potassium chloride and 0.15 grams methyl p-hydroxybenzoate preservative and added to 177 ml water. The solution is heated to 90° C. to dissolve; cooled to 60° C., and a blend of 6.0 grams peppermint oil fragrance, 8.0 grams isopropanol, and 4.0 grams ethylene glycol is added. The solution is placed in plastic molds and cooled to ambient temperature. A strong, brittle gel with heavy mint fragrance forms. The gel can be unmolded easily and retains its shape without sagging.

EXAMPLE 8

Comparison of Native, Deacetylated, and Clarified and Deacetylated S-60

Three samples of S-60 (native, deacetylaed, and deacetylated and clarified) are analyzed. The following data are obtained.

| | Native | Deacetylated | Deacetylated and clarified |
|---|---|---|---|
| Uronic acid (%) | 11 | 13 | 22 |
| Acetyl (%) | 3.0 | 0 | 0 |
| Neutral sugar (% mol. ratio) | | | |
| Glucose | (40) | (40) | (40) |
| Rhamnose | (60) | (60) | (60) |
| Proteins | 10 | 17 | 2 |
| Ash | 7.0 | 8.0 | 9.5 |

What is claimed is:

1. Deacetylated heteropolysaccharide S-60, which comprises (a) about 50% (wt./wt.) insoluble material of which about 34% (wt./wt.) is protein, and (b) about 50% (wt./wt.) carbohydrate which contains about 22-26% (wt./wt.) glucuronic acid, 0% acetyl groups, and the neutral sugars rhamnose and glucose in the approximate molar ratio 3:2, said rhamnose and glucose sugars being primarily 1,4 β-linked, said heteropolysaccharide being further characterized in that it is anionic, and forms brittle, thermoreversible gels.

2. A process for preparing the compound of claim 1 which comprises heating a 1-5% aqueous solution of the heteropolysaccharide S-60 at a pH of about 10, at a temperature of 90°-100° C. for from 10 minutes to 45 minutes, and recovering the product thereby produced.

3. Deacetylated heteropolysaccharide S-60 produced by a process which comprises heating a 1-5% aqueous solution of heteropolysaccharide S-60 at a pH of about 10, at a temperature of 90°-100° C. for from 10 minutes to 45 minutes, and recovering the product thereby produced.

4. Deacetylated, clarified heteropolysaccharide S-60, which comprises no more than about 2% (wt./wt.) protein and carbohydrate said carbohydrate containing about 22-26% (wt./wt.) glucoronic acid, 0% acetyl groups, and the neutral sugars rhamnose and glucose in the approximate molar ratio 3:2, said rhamnose and glucose sugars being primarily 1,4 β-linked, said heteropolysaccharide being further characterized in that it is anionic, and forms brittle, thermoreversible gels.

* * * * *